(12) United States Patent
Niimi et al.

(10) Patent No.: US 11,076,839 B2
(45) Date of Patent: Aug. 3, 2021

(54) ULTRASONIC INSPECTION PHANTOM AND METHOD OF MANUFACTURING SAME

(71) Applicants: Tatsuya Niimi, Kanagawa (JP); Takashi Matsumura, Kanagawa (JP); Takuya Saito, Kanagawa (JP)

(72) Inventors: Tatsuya Niimi, Kanagawa (JP); Takashi Matsumura, Kanagawa (JP); Takuya Saito, Kanagawa (JP)

(73) Assignee: Ricoh Company, Ltd., Tokyo (JP)

(*) Notice: Subject to any disclaimer, the term of this patent is extended or adjusted under 35 U.S.C. 154(b) by 149 days.

(21) Appl. No.: 16/202,177

(22) Filed: Nov. 28, 2018

(65) Prior Publication Data

US 2019/0175151 A1    Jun. 13, 2019

(30) Foreign Application Priority Data

Dec. 7, 2017  (JP) .............................. JP2017-235245

(51) Int. Cl.
*A61B 8/00*      (2006.01)
*G09B 23/28*    (2006.01)
*A61B 17/34*    (2006.01)

(52) U.S. Cl.
CPC ............ *A61B 8/587* (2013.01); *G09B 23/286* (2013.01); *A61B 2017/3413* (2013.01)

(58) Field of Classification Search
None
See application file for complete search history.

(56) References Cited

U.S. PATENT DOCUMENTS

| | | | |
|---|---|---|---|
| 4,958,626 A * | 9/1990 | Nambu | A61K 41/0028 601/3 |
| 2008/0261009 A1 | 10/2008 | Kawabata | |
| 2015/0164463 A1* | 6/2015 | Oraevsky | A61B 5/0095 73/866.4 |
| 2016/0275818 A1* | 9/2016 | Norikane | A61B 34/00 |
| 2017/0239886 A1 | 8/2017 | Norikane | |
| 2018/0061279 A1 | 3/2018 | Niimi et al. | |
| 2018/0126651 A1 | 5/2018 | Matsumura et al. | |
| 2018/0272615 A1 | 9/2018 | Norikane et al. | |

FOREIGN PATENT DOCUMENTS

| | | |
|---|---|---|
| JP | 08-010254 | 1/1996 |
| JP | 2011-057962 | 3/2011 |
| JP | 2015-138192 | 7/2015 |
| WO | WO2005/107599 A1 | 11/2005 |
| WO | WO2010/016353 A1 | 2/2010 |

(Continued)

OTHER PUBLICATIONS

Sijing Xiong, et al. Specific surface area of titanium dioxide (TiO2) particles influences cyto- and photo-toxicity, Toxicology, vol. 304, 2013, pp. 132-140. https://doi.org/10.1016/j.tox.2012.12.015. (Year: 2013).*

(Continued)

*Primary Examiner* — Paul M. West
*Assistant Examiner* — Mark A Shabman
(74) *Attorney, Agent, or Firm* — Oblon, McClelland, Maier & Neustadt, L.L.P.

(57) ABSTRACT

An ultrasonic inspection phantom includes ultrasonic inspection phantom including a hydrogel including water, a polymer, and a mineral.

21 Claims, 5 Drawing Sheets

DISPERSED IN WATER

(56) References Cited

FOREIGN PATENT DOCUMENTS

WO    WO-2015111366 A1 *  7/2015  ............. C08K 3/346

OTHER PUBLICATIONS

Extended European Search Report dated Mar. 1, 2019 in the corresponding European Application No. 18207050.8 9 pages.
Culjat, M. O., et al., "A Review of Tissue Substitutes for Ultrasound Imaging", Ultrasound in Medicine and Biology., vol. 36, No. 6, XP055559425, 2010, pp. 861-873.
Tsuchida, T., "Preparation of high surface area cu-$Al_2$, $O_3$, and its surface properties", Applied Catalysis A: General, vol. 105, XP055559675, 1993, L141-L146.
Anonymous: "Self-healing hydrogels—Wikipedia", URL:https://en.wikipedia.org/w/index.php?title=Self-healing_hydrogels&oldid=813384126, XP055559852, Dec. 3, 2017, 12 pages.

* cited by examiner

ULTRASONIC INSPECTION PHANTOM AND METHOD OF MANUFACTURING SAME

CROSS-REFERENCE TO RELATED APPLICATIONS

This patent application is based on and claims priority pursuant to 35 U.S.C. § 119 to Japanese Patent Application No. 2017-235245, filed on Dec. 7, 2017, in the Japan Patent Office, the entire disclosures of which are hereby incorporated by reference herein.

BACKGROUND

Technical Field

The present disclosure relates to an ultrasonic inspection phantom and a method of manufacturing the ultrasonic inspection phantom.

Description of the Related Art

Lesions caused in human organs are examined by an ultrasonic inspection device. In addition, for training using an ultrasonic inspection device in advance, an ultrasonic inspection phantom mimicking living tissue is used.

As the material constituting an ultrasonic inspection phantom, for example, polyvinyl alcohol has been proposed, a polyacrylamide-containing gel has been proposed, and a gelated material including transparent silicone gel acrylic-based resin as one of the materials has been proposed.

SUMMARY

According to the present invention, provided is an improved ultrasonic inspection phantom which includes a hydrogel comprising water, a polymer, and a mineral.

BRIEF DESCRIPTION OF THE SEVERAL VIEWS OF THE DRAWINGS

A more complete appreciation of the embodiments and many of the attendant advantages and features thereof can be readily obtained and understood from the following detailed description with reference to the accompanying drawings, wherein.

Figure 1:
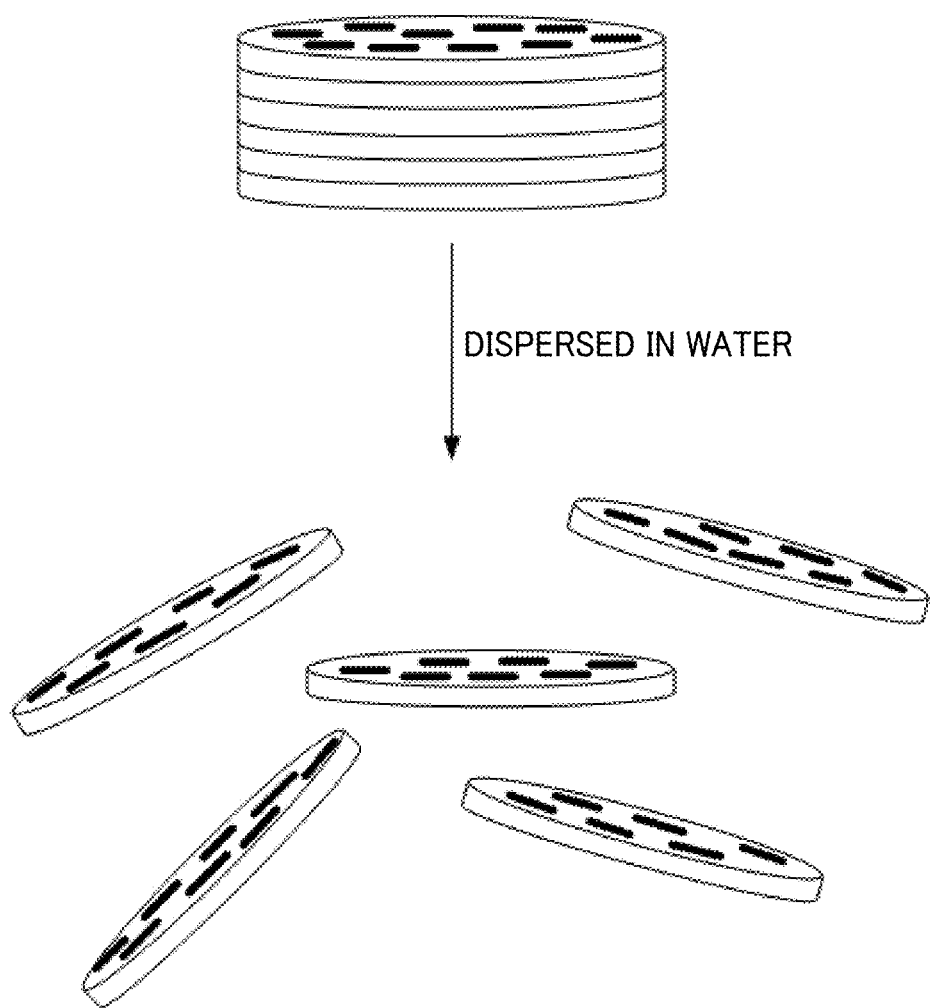
FIG. 1 is a schematic diagram illustrating an example of a water-swellable laminate clay mineral as a mineral and an example of a state in which a water-swellable laminate clay mineral is dispersed in water.

The accompanying drawings are intended to depict embodiments of the present invention and should not be interpreted to limit the scope thereof. The accompanying drawings are not to be considered as drawn to scale unless explicitly noted. Also, identical or similar reference numerals designate identical or similar components throughout the several views.

DESCRIPTION OF THE EMBODIMENTS

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

As used herein, the singular forms "a", "an", and "the" are intended to include the plural forms as well, unless the context clearly indicates otherwise.

Moreover, image forming, recording, printing, modeling, etc. in the present disclosure represent the same meaning, unless otherwise specified.

According to the present disclosure, an ultrasonic inspection phantom is provided which has real texture suitable for training of ultrasonic inspection procedures and excellent handling property.

Ultrasonic Inspection Phantom

The ultrasonic inspection phantom of the present disclosure includes a hydrogel including water, a polymer, a mineral, and other optional components.

The ultrasonic inspection device typically includes a probe to generate (transmits) ultrasonic waves and receive ultrasonic waves (echoes) reflected at a lesion, a processing unit to process the received data via the prove, and a monitor (display) to display the data processed by the processing unit as an image.

In the lesion inspection using an ultrasonic inspection device, for example, the lesion part is subjected to a treatment such as puncturing with a puncture needle while observing a lesion part image displayed on the monitor.

It is desirable to conduct a puncture treatment with a puncture needle in advance using an ultrasonic inspection phantom mimicking a living tissue. The ultrasonic inspection phantom deserving such training satisfies the following properties and features: (1) an image under ultrasonic guidance is similar to the image of an actual living tissue; (2) a normal part is clearly distinguishable from a lesion; (3) it is possible to collect components of a lesion by a puncture needle, etc.; (4) tactile sensation (texture) obtained when punctured with a puncture needle, etc. is similar to tactile sensation of a human body, and (5) it is possible to stand repetitive use, if possible.

Therefore, in the present disclosure, it is possible to provide an ultrasonic inspection phantom including a hydrogel containing water, a polymer, and a mineral and having the properties necessary for training under ultrasonic guidance with excellent handling property. Further, according to the present disclosure, it is possible to provide an ultrasonic inspection phantom that can be repeatedly subjected to puncture treatment, etc.

The ultrasonic inspection phantom is preferably made of a hydrogel enclosing water in a three-dimensional network structure of a complex combination of a mineral dispersed in a solvent and a polymer polymerized of a polymerizable monomer.

Polymer

As the polymer, polymers having, for example, an amide group, an amino group, a hydroxyl group, a tetramethyl ammonium group, a silanol group, an epoxy group, etc. are suitable and allowed to be water-soluble.

Water-solubility of the polymer in the present disclosure means, for example, when 1 g of a polymer is mixed with and stirred in 100 g of water at 30 degrees C., 90 percent by mass or more of the polymer is dissolved in water.

The polymer can be a homopolymer (monopolymer) and heteropolymers (copolymers). These can be modified and known functional groups can be introduced into these. Forms of salts are also allowed.

Polymers are obtained by polymerizing polymerizable monomers.

Water

As the water, pure water and hyper pure water such as deionized water, ultrafiltered water, reverse osmosis water, and distilled water can be used.

It is suitable to dissolve or disperse other components such as organic solvents in the water to impart moisturizing property, antibiotic property, or electroconductive property and adjust hardness.

Mineral

The mineral has no particular limit and can be suitably selected to suit to a particular application. For example, water swellable laminate clay minerals are suitable. For example, FIG. 1 is a schematic diagram illustrating an example of a water-swellable laminate clay mineral as a mineral and an example of a state in which a water-swellable laminate clay mineral is dispersed in water.

As illustrated in the upper diagram in FIG. 1, the water-swellable laminate clay mineral is dispersed in water in a single layer state and assumes a state in which two-dimensional disk-like crystals having unit cells in the crystal are stacked. Further, when the water-swellable laminate clay mineral in the upper diagram of FIG. 1 is dispersed in water, each single layer is separated into a plurality of two-dimensional disc-like crystals as illustrated in the lower diagram in FIG. 1.

Examples of such clay minerals are water swellable smectite and water swellable mica. Specific examples include, but are not limited to, water swellable hectorite containing sodium as an interlayer ion, water swellable montmorillonite, water swellable saponite, and water swellable synthesized mica. These can be used alone or in combination. Of these, water-swellable hectorite is preferable to obtain an ultrasonic inspection phantom with high elasticity.

Water swellable hectorite can be appropriately synthesized or is available on the market. Specific examples of the product available on the market include, but are not limited to, synthesized hectorite (laponite XLG, manufactured by Rockwood Additives Ltd.), SWN (manufactured by Coop Chemical Ltd.), and fluorinated hectorite SWF (manufactured Coop Chemical Ltd.). Of these, synthetic hectorite is preferable in terms of elastic modulus of the ultrasonic inspection phantom.

"Water swellable" means that water molecules are inserted between each layer of the laminate clay mineral and each layer is dispersed in water as illustrated in FIG. 1.

The amount of the mineral is preferably from 1 to 40 percent by mass, more preferably from 1 to 25 percent by mass to the total amount of the ultrasonic inspection phantom in terms of elastic modulus and hardness of the ultrasonic examination phantom.

Organic Solvent

The organic solvent is contained to enhance the moisture retention of the ultrasonic inspection phantom.

Specific examples of the organic solvent include, but are not limited to, alkyl alcohols having one to four carbon atoms such as methyl alcohol, ethyl alcohol, n-propyl alcohol, isopropyl alcohol, n-butyl alcohol, sec-butyl alcohol, and tert-butyl alcohol, amides such as dimethylformamide and dimethylacetoamide, ketones or ketone alcohols such as acetone, methylethylketone, and diacetone alcohol, ethers such as tetrahydrofuran and dioxane, polyols such as ethylene glycol, propylene glycol, 1,2-propane diol, 1,2-butane diol, 1,3-butane diol, 1,4-butane diol, diethylene glycol, triethylene glycol, 1,2,6-hexane triol, thioglycol, hexylene glycol, and glycerin, polyalkylene glycols such as polyethylene glycol and polypropylene glycol, lower alcohol ethers of polyols such as ethylene glycol monomethyl (or ethyl) ether, diethylene glycol methyl (or ethyl) ether, and triethylene glycol monomethyl (or ethyl) ether, alkanol amines such as monoethanol amine, diethanol amine, and triethanol amine, N-methyl-2-pyrolidone, 2-pyrolidone, 1,3-dimethyl-2-imidazoline. These can be used alone or in combination. Of these, in terms of moisture retention, polyols are preferable and glycerin and propylene glycol are more preferable.

The amount of the organic solvent is preferably from 10 to 50 percent by mass to the total amount to the ultrasonic inspection phantom. When the amount of the organic solvent is 10 percent by mass or greater, the effect of anti-drying can be demonstrated. When the amount of the organic solvent is 50 percent by mass or less, the laminate clay mineral is uniformly dispersed.

Metal Oxide

It is preferable to add metal oxide particles to the ultrasonic inspection phantom of the present disclosure to control the ultrasonic wave propagation speed of an ultrasonic inspection device. This is because the metal oxide particle scatters ultrasonic waves, thereby providing contrast to an ultrasonic images (echo images).

Since the metal oxide is used as a scatterer, a larger contact interface between the particle and the surrounding material is advantageous. Preferably, the metal oxide particle has a specific surface area of 50 $m^2/g$ or greater. The specific surface area of the metal oxide is more preferably from 50 to 250 $m^2/g$.

The specific surface area can be measured by, for example, a gas adsorption method (BET method).

As the metal oxide, when the specific surface area is 50 $m^2/g$ or greater, it can be suitably selected to suit to a particular application. Examples include silica, alumina-containing silica, alumina, titanium oxide, zinc oxide, zirconia, or a metal oxide composite. These can be used alone or in combination. Of these, silica and alumina-containing silica are preferable.

Since these metal oxides are dispersed in the hydrogel, it is suitable to use a particle having a hydrophilic surface.

The amount of the metal oxide is preferably from 1 to 5 percent by mass to the total amount to the ultrasonic inspection phantom.

Other Components

The other optional components have no particular limit and can be suitably selected to suit to a particular application. For example, such other optional components include a phosphonic acid compound such as 1-hydroxyethane-1,1-diphosphonic acid, stabilizers, surfactants, polymerization initiators, colorants, viscosity modifiers, adhesion imparting agents, antioxidants, anti-aging agents, cross-linking promoters, ultraviolet absorbents, plasticizers, preservatives, and dispersants.

Since the major components of the hydrogel for use in the present disclosure are the polymer and water, it is close to the composition of the human body in the first place, so that the propagation velocity of the ultrasonic wave is close to the value of the human body.

In the human body, cavities filled with body fluids and regions rich in water composition appear black in an ultrasound image (echo image). These also appear black in a simple hydrogel. Bones and lipid regions appear white, and various organs, etc. appear intermediate between black and white.

Addition of a suitable amount of metal oxide to the hydrogel makes it possible to arbitrarily control ultrasonic propagation speed and provide a contrast in an ultrasonic image. Without an addition of a metal oxide to the hydrogel, the echo image appears black. However, as the addition amount of the metal oxide to the hydrogel increases, the echo image shifts from gray to white.

Since the ultrasonic inspection phantom of the present disclosure is used for training of puncture treatment of ultrasonic inspection, the ultrasonic inspection phantom preferably includes a pseudo lesion mimicking a lesion caused in living tissue.

It is preferable that the ultrasonic propagation in the pseudo lesion be slower than in the ultrasonic inspection phantom.

The pseudo lesion preferably contains a metal oxide having a specific surface area of 150 $m^2/g$ or greater.

As the metal oxide, as long as the specific surface area is 150 $m^2/g$ or greater, it can be suitably selected to suit to a particular application. Examples include silica, alumina-containing silica, alumina, titanium oxide, zinc oxide, zirconia, or a metal oxide composite. These can be used alone or in combination. Of these, silica and alumina-containing silica are preferable.

The ultrasonic inspection phantom of the present disclosure includes a hydrogel in which a mineral is added to a polymer and water. Due to this addition of mineral, this hydrogel has the following two features over a typical hydrogel.

The first feature is controlling strength and toughness. Since the content ratio of the polymer and the mineral against water in the hydrogel in the present disclosure can be changed, the texture can be made close to the texture of a target organ, which provides a real feeling during training.

The second feature is imparting self-healing property. When the hydrogel is used for training of puncturing, the site at which a specimen is enucleated by the puncture treatment gets a hole. Therefore, typical phantoms are not reusable. Conversely, due to the acting of the polymer network formed between the mineral layers, the hydrogel included in the present disclosure is restored as the severed network is restored over time. Therefore, the phantom once used can be repeatedly used.

Moreover, precursors of the ultrasonic inspection phantom of the present disclosure can be directly fabricated by a 3D printer. For this reason, it is possible to arbitrarily fabricate a specific target form, etc.

The hydrogel used in the present disclosure is an extremely optimal material because it demonstrates the features never realized as the material for the ultrasonic inspection phantom.

Method of Manufacturing Ultrasonic Inspection Phantom

In the method of manufacturing the ultrasonic inspection phantom of the present disclosure, a liquid material for forming a phantom containing water, a mineral, and a polymerizable monomer is used.

Liquid Material for Forming Phantom

The liquid material for forming a phantom contains water, a mineral, and a polymerizable monomer. Optionally, the liquid material contains an organic solvent, a metal oxide, and further other components.

As the water, mineral, organic solvent, metal oxide, and other components, the same as for the ultrasonic inspection phantom can be used.

Polymerizable Monomer

The polymerizable monomer is a compound having at least one unsaturated carbon-carbon bond and includes, for example, a mono-functional monomer and a multi-functional monomer. Furthermore, the multi-functional monomer includes a bi-functional monomer, a tri-functional monomer, or a tetra- or higher functional monomer.

The mono-functional monomer is a compound having a single unsaturated carbon-carbon bond. Examples are acrylamides, N-substituted acrylamide derivatives, N,N-di-substituted acrylamide derivatives, N-substituted methacrylamide derivatives, N,N-di-substituted methacrylamide derivatives, and other mono-functional monomers. These can be used alone or in combination.

The N-substituted acrylamide derivatives, N,N-di-substituted acrylamide derivatives, N-substituted methacrylamide derivatives, and N,N-di-sub stituted methacryl amide derivatives include, for example, N,N-dimethyl acryl amide (DMAA) and N-isopropyl acryl amide. Specific examples of the other mono-functional monomers include, but are not limited to, 2-etylhexyl(meth)acrylate (EHA), 2-hydroxyethyl(meth)acrylate (HEA), 2-hydroxypropyl(meth)acrylate (HPA), acryloyl morpholine (ACMO), caprolactone-modified tetrahydrofurfuryl(meta)acrylate, isobonyl(meth)acrylate, 3-methoxybutyl(meth)acrylate, tetrahydro furfuryl (meth)acrylate, lauryl(meth)acrylate, 2-phenoxyethyl(meth)acrylate, isodecyl(meth)acrylate, isooctyl(meth)acrylate, tridecyl(meth)acrylate, caprolactone(meth)acrylate, ethoxyfied nonylphenol(meth)acrylate, and urethane(meth)acrylate. These can be used alone or in combination.

Water-soluble organic polymers having an amide group, an amino group, a hydroxyl group, a tetramethyl ammonium group, a silanol group, an epoxy group, etc. are obtained by polymerizing mono-functional monomers.

Water soluble organic polymers having an amide group, an amino group, a hydroxyl group, a tetramethyl ammonium group, a silanol group, an epoxy group, etc. are advantageous to maintain the strength of an ultrasonic inspection phantom.

The amount of the mono-functional monomer is not particularly limited but can be suitably selected to suit to a particular application. It is preferably from 1 to 10 percent by mass and more preferably from 1 to 5 percent by mass to the total amount of the liquid material for forming a phantom. When the amount of the mono-functional monomer is in the range of from 1 to 10 percent by mass, dispersion stability of a laminate clay mineral in the liquid material for forming a phantom is maintained and stretchability of the ultrasonic inspection phantom is enhanced. Stretchability means that when an ultrasonic inspection phantom is stretched, the ultrasonic inspection phantom is not fractured (broken) but stretched.

Specific examples of the bi-functional monomer include, but are not limited to, tripropylene glycol di(meth)acrylate, triethylene glycol di(meth)acrylate, tetraethylene glycol di(meth)acrylate, polypropylene glycol di(meth)acrylate, neopentyl glycol hydroxy pivalic acid ester di(meth)acrylate (MANDA), hydroxypivalic acid neopentyl glycol ester di(meth)acrylate (HPNDA), 1,3-butane diol di(meth)acrylate (BGDA), 1,4-butane diol di(meth)acrylate (BUDA), 1,6-hexane diol di(meth)acrylate (HDDA), 1,9-nonane diol (meth)acrylate, diethylene glycol di(meth)acrylate (DEGDA), neopentyl glycol di(meth)acrylate (NPGDA), tripropylene glycol di(meth)acrylate (TPGDA), caprolactone-modified hydroxy pivalic acid neopentyl glycol ester di(meth)acrylate, propoxinated neopentyl glycol di(meth)acrylate, ethoxy-modified bisphenol A di(meth)acrylate, polyethylene glycol 200 di(meth)acrylate, polyethylene glycol 400 di(meth)acrylate, and methylenebis acrylamide. These can be used alone or in combination.

Specific examples of the tri-functional monomers include, but are not limited to, trimethylol propane tri(meth)acrylate (TMPTA), pentaerythritol tri(meth)acrylate (PETA), triallyl isocyanate, tris(2-hydroxyethyl)isocyanulate tri(meth)acrylate, ethoxyfied trimethylol propane tri(meth)acrylate, propoxyfied trimethylol propane tri(meth)acrylate, and propoxyfied glyceryl tri(meth)acrylate. These can be used alone or in combination.

Specific examples of the tetra- or higher functional monomers include, but are not limited to, pentaerythritol tetra (meth)acrylate, ditrimethylol prop anetetra(meth)acrylate, dipentaerythritol hydroxypenta(meth)acrylate, ethoxyfied pentaerythritol tetra (meth)acrylate, penta(meth)acrylate ester, and dipentaerythritol hexa(meth)acrylate (DPHA). These can be used alone or in combination.

The proportion of the multi-functional monomer is preferably from 0.001 to 1 percent by mass and more preferably from 0.01 to 0.5 percent by mass to the total content of the liquid material for forming a phantom. When the proportion is from 0.001 to 1 percent by mass, elasticity modulus and hardness of an obtained solid ultrasonic inspection phantom can be controlled within suitable ranges.

It is preferable to harden the liquid material for forming a phantom using a polymerization initiator. The polymerization initiator is added to the liquid material for forming a phantom.

Polymerization Initiator

Examples of the polymerization initiator are thermal polymerization initiators and photopolymerization initiators.

The thermal polymerization initiator has no particular limitation and can be suitably selected to suit to a particular application. Examples thereof are azo-based initiators, peroxide initiators, persulfate initiators, and redox (oxidation-reduction) initiators.

Specific example of the azo-based initiator include, but are not limited to, VA-044, VA-46B, VA-50, VA-057, VA-061, VA-067, VA-086, 2,2'-azobis(4-methoxy-2,4-dimethylvaleronitrile) (VAZO® 33), 2,2'-azobis(2-amidinopropane)dihydrochloride (VAZO® 50), 2,2'-azobis(2,4-dimetaylvaleronitrile) (VAZO® 52), 2,2'-azobis(isobutylonitrile) (VAZO® 64), 2,2'-azobis-2-methylbutylonitrile) (VAZO® 67), and 1,1-azobis(1-cyclohexane carbonitrile) (VAZO® 88) (all available from E.I. du Pont de Nemours and Company), 2,2'-azobis(2-cyclopropylpropionitrile), and 2,2'-azobis(methylisobutylate) (V-601) (all available from FUJIFILM Wako Pure Chemical Corporation).

Specific examples of the peroxide initiator include, but are not limited to, benzoyl peroxide, acetyl peroxide, lauroyl peroxide, decanoyl peroxide, dicetyl peroxy dicarbonate, di(4-t-butylcyclohexyl)peroxy dicarbonate (Perkadox 16S) (available from Akzo Nobel N.V.), di(2-ethylhexyl)peroxy dicarbonate, t-butyl peroxypivalate (Lupersol 11) (all available from Elf Atochem S.A), t-butylperoxy-2-ethyl hexanoate (Trigonox 21-050) (available from Akzo Nobel N.V), and dicumyl peroxide.

Specific examples of the persulfate initiator include, but are not limited to, potassium persulfate, sodium persulfate, ammonium persulfate, and peroxo sodium disulfate.

Specific examples of redox (oxidation-reduction) initiator include, but are not limited to, a combination of the persulfate initiator and a reducing agent such as sodium metabisulfite and sodium bisulfite, a system based on the organic peroxide and tertiary amine (such as a system based on benzoyl peroxide and dimethylaniline), and a system based on organic hydroperoxide and transition metal (such as a system based on cumenhydroperoxide and cobalt naftate).

As the photopolymerization initiator, any material can be used which produces a radical upon irradiation of light (ultraviolet rays in a wavelength range of 220 to 400 nm).

Specific examples of the photopolymerization initiator include, but are not limited to, acetophenone, 2,2-diethoxyacetophenone, p-dimethylaminoacetophenone, benzophenone, 2-chlorobenzophenone, p,p'-dichlorobenzophenone, p,p-bisdiethylamonobenzophenoen, Michler's Ketone, benzyl, benzoin, benzoin methylether, benzoin ethylether, benzoin isopropylether, benzoin-n-propyl ether, benzoin isobutyl ether, benzoin-n-butylether, benzylmethyl ketal, thioxanthone, 2-chlorothioxanthone, 2-hydroxy-2-methyl-1-phenyl-1-one, 1-(4-isopropylphenyl)-2-hydroxy-2-methylpropane-1-one, methylbenzoyl formate, 1-hydroxy cyclohexyl phenylketone, azobisisobutylo nitrile, benzoylperoxide, and di-tert-butylperoxide. These can be used alone or in combination.

Incidentally, tetramethylethylenediamine is used as an initiator of polymerization/gelation reaction to turn acrylamide into a polyacrylamide gel.

The method of manufacturing the ultrasonic inspection phantom of the present disclosure is roughly classified into a method using a mold and a direct manufacturing method using a three-dimensional printer.

Method of Manufacturing Using Mold

In the method using a mold, the liquid material for forming a phantom is poured into a mold and hardened.

Figure 2:
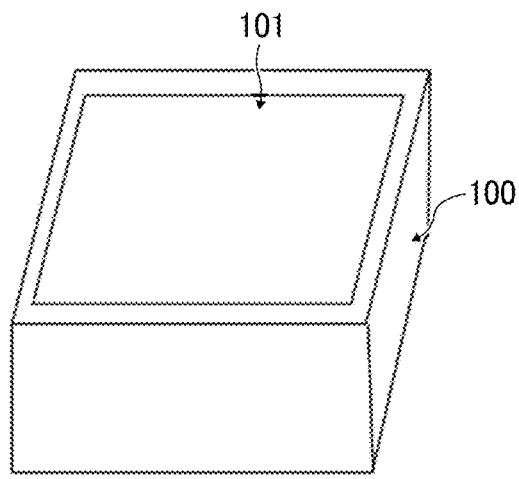
FIG. 2 is a schematic diagram illustrating an example of a mold used for molding the ultrasonic inspection phantom of the present disclosure.

To manufacture an ultrasonic inspection phantom having a desired form, a mold having the desired form is prepared. For example, for a cuboid 101 as illustrated in FIG. 2 or a cylinder 102 as illustrated in FIG. 3, a corresponding mold is prepared and the liquid material for forming a phantom is infused into the mold.

To harden the liquid material using a thermal polymerization initiator, the reaction temperature is controlled depending on the kind of the initiator. The liquid material for forming a phantom is poured into the mold, and the mold is sealed to block the phantom from air (oxygen) to allow polymerization reaction at room temperature or a predetermined temperature.

Figure 4:
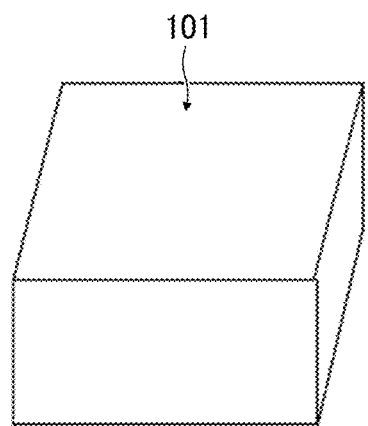
FIG. 4 is a schematic diagram illustrating an example of the ultrasonic inspection phantom of the present invention taken out of a mold.

After completion of the polymerization, the cuboid (phantom) 101 is taken out of the mold (see FIG. 4).

Figure 3:
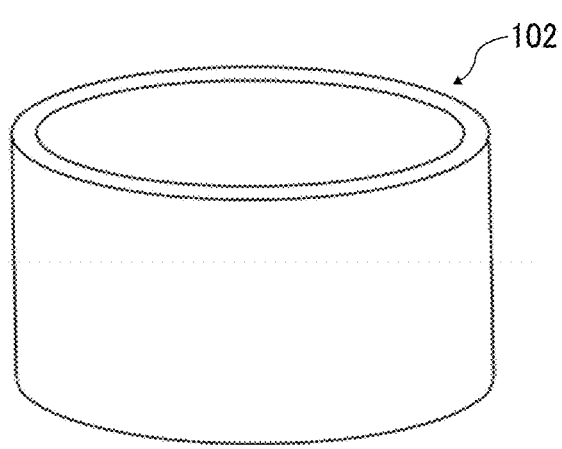
FIG. 3 is a schematic diagram illustrating another example of a mold used for molding the ultrasonic inspection phantom of the present disclosure.

Further, to form a part having a different composition (i.e., having different ultrasonic wave propagation speed) inside, a fabricated part 104 is separately set in a mold as illustrated in FIG. 3, and a liquid material for forming a phantom is poured and hardened. As a result, as illustrated in FIG. 5, an ultrasonic inspection 103 having the part having a different composition (i.e., having different ultrasonic wave propagation speed) inside is formed.

To harden the liquid material for forming a phantom using a photopolymerization initiator, a hardening device is used to irradiate the liquid material with energy rays such as ultraviolet rays. Therefore, the mold to be used is made of a material transparent to energy rays. The liquid material is poured into such a mold, which is thereafter sealed to block from air (oxygen). Subsequently, the mold is irradiated with energy rays from outside.

After completion of the polymerization, the content (a phantom 103) is taken out of the mold.

Figure 5:
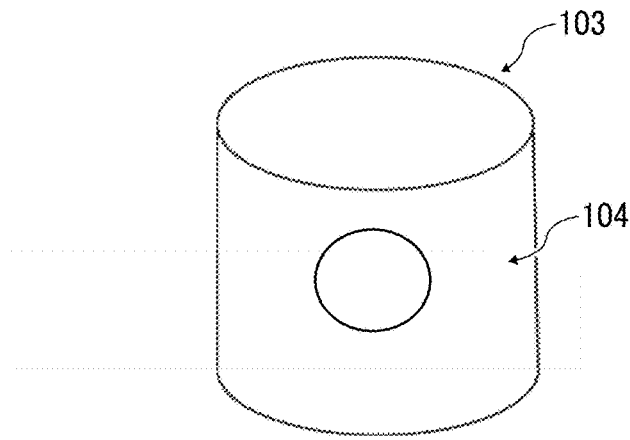
FIG. 5 is a schematic diagram illustrating another example of the ultrasonic inspection phantom of the present disclosure.

Unlike the ultrasonic inspection phantoms having relatively simple forms as illustrated in FIGS. 4 and 5, for example, to form an ultrasonic inspection phantom having an outlook mimicking the form of an internal organ, it is preferable to manufacture a mold using a 3D printer.

The 3D printer is not particularly limited. However, since a liquid material for forming a phantom is poured into a mold and hardened, it is preferable to employ inkjet (material jet) methods, stereolithography, laser sintering methods to form an ultra inspection phantom in terms of preventing leakage of the liquid material.

For example, to prepare a mold conforming to the form of an internal organ, the computed tomography (CT) data is acquired and converted into three-dimensional (3D) data so that a male and female mold can be produced based on the CT data. Based on this 3D data, an ultrasonic inspection phantom is directly manufactured using a 3D printer.

It is preferable that the liquid material for forming a phantom be poured into a mold prepared by a 3D printer based on desired form data and hardened to form a phantom.

Method of Direct Forming Using 3D Printer

A phantom is directly fabricated by a 3D printer using a liquid material for forming a phantom.

It is preferable that the 3D printer employ an inkjet method or stereolithography. By these methods, it is possible to control a composition distribution and a form, thereby forming an ultrasonic inspection phantom having a desired form and properties.

The 3D printer is preferable to employ a method capable of printing a material of a phantom. It includes, for example, an inkjet (material jet) method or dispenser method of discharging ink and hardening the ink upon application of UV light. In these methods, since a plurality of materials for forming the ultrasonic inspection phantom can be used, it is possible to provide a distribution to the composition constituting an ultrasonic inspection phantom instead of forming the ultrasonic inspection phantom with a single composition for the entire of the ultrasonic inspection phantom. In particular, it is possible to provide a composition distribution that can control the propagation speed of ultrasonic waves. This is an effective technique to reproduce a part which is not a normal cell.

Figure 6:
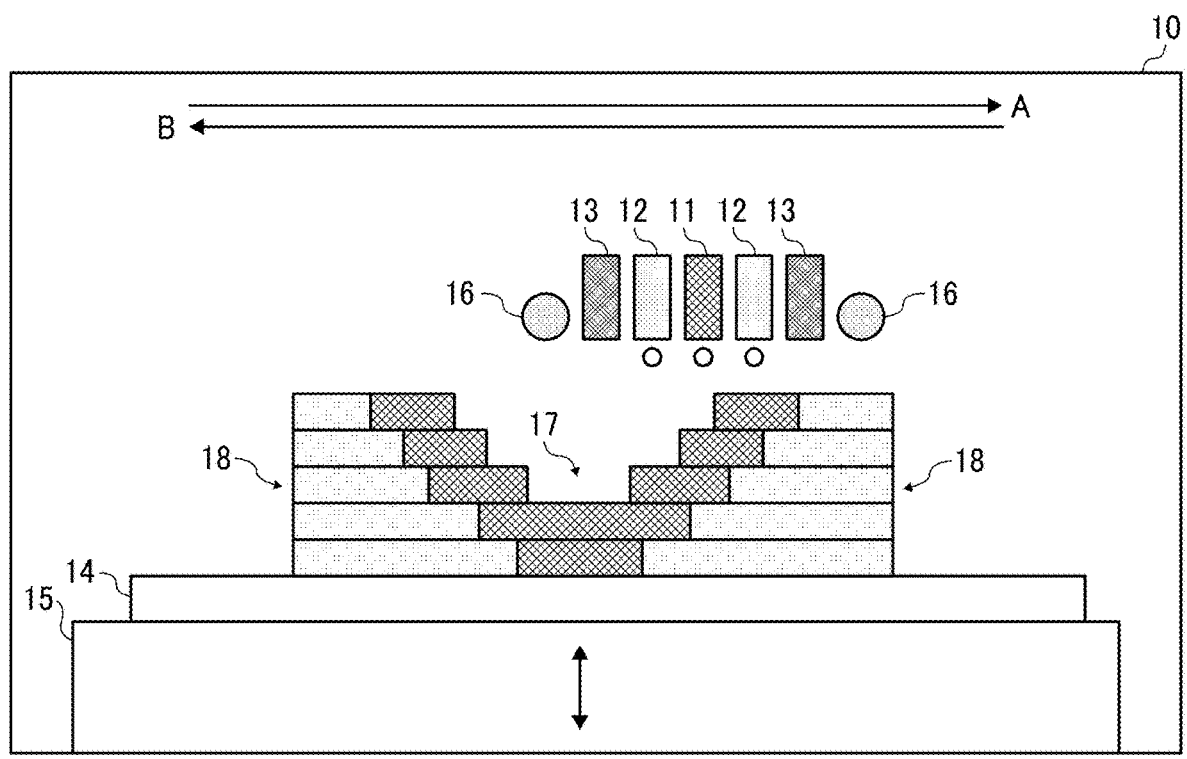
FIG. 6 is a schematic diagram illustrating a 3D printer to fabricate an ultrasonic inspection phantom.

For example, FIG. 6 is a diagram illustrating a 3D printer 10 employing an inkjet (IJ) method. The 3D printer 10 includes head units including inkjet heads arranged inside. A head unit 11 jetting a liquid material for fabrication discharges a liquid material for forming a phantom and a head unit 12 jetting a liquid material for forming a support discharges a liquid material for forming a support. An ultraviolet irradiator 13 disposed adjacent to the head unit 12 irradiates the liquid material for forming a phantom and the liquid material for forming a support to harden these materials to form a layer. This operation is repeated to laminate layers. Furthermore, the 3D printer 10 includes a support substrate 14 for a fabrication object and a smoothing member 16.

To keep the gap between the head unit 11, the head unit 12, and the ultraviolet irradiator 13 and a fabrication object (ultrasonic inspection phantom) 17 and a support 18, a stage 15 is lowered for lamination in accordance with the number of lamination.

In the 3D printer 10, the ultraviolet irradiators 13 are used in both directions indicated by arrows A and B. Due to the heat generated upon application of ultraviolet rays, the surface of the liquid material for forming a support is smoothed, thereby improving the dimension stability of an ultrasonic inspection phantom.

Figure 7:
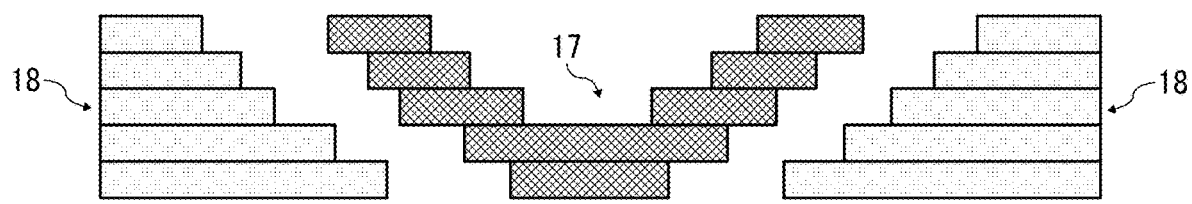
FIG. 7 is a schematic diagram illustrating a state in which a support material is peeled off from an ultrasonic inspection phantom fabricated by a 3D printer.

After the fabrication is completed, as illustrated in FIG. 7, the ultrasonic inspection phantom 17 and the support 18 are pulled in the horizontal direction and detached from each other in such a manner that the support 18 is detached as a whole, that is, the ultrasonic inspection phantom 17 can be easily obtained.

Figure 8:
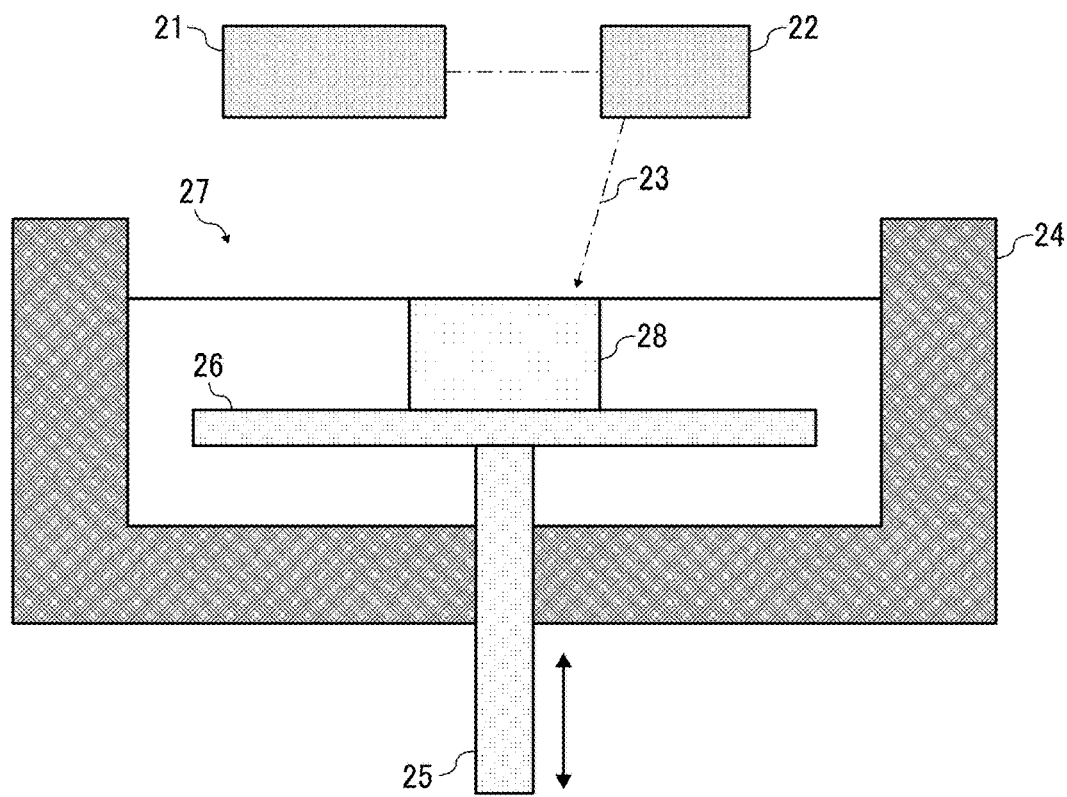
FIG. 8 is a schematic diagram illustrating a 3D printer employing another method to fabricate an ultrasonic inspection phantom.

In addition, the 3D printer employing stereolithography as illustrated in FIG. 8 stores a liquid material for forming a phantom in a liquid pool 24, irradiates a surface 27 of the liquid pool 24 with ultraviolet laser beams 23 emitted from a laser light source 21 via a laser scanner 22 to form a hardened article on a fabrication stage 26. The fabrication stage 26 lowers by the action of a piston 25. These operations are sequentially repeated to form a fabrication object (ultrasonic inspection phantom) 28.

Having generally described preferred embodiments of this disclosure, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Next, the present disclosure is described in detail with reference to Examples but is not limited thereto.

Preparation Example 1

Preparation of Liquid Material 1 for Forming Phantom

First, while stirring 700 parts of deionized water, 13 parts of synthetic hectorite (Laponite XLG, manufactured by Rockwood Additives Ltd.) having a composition of $[Mg_{5.34}Li_{0.66}Si_8O_{20}(OH)_4]$ $Na^-_{0.66}$ as a mineral was added to the deionized water little by little and 0.6 parts of 1-hydroxyethane-1,1-diphosphonic acid was further added thereto followed by stirring to prepare a liquid dispersion.

Next, 7 parts of N, N-dimethylacrylamide as a polymerizable monomer (manufactured by FUJIFILM Wako Pure Chemical Corporation) which was caused to pass through a column of activated alumina to remove the polymerization inhibitor, 35 parts of acryloyl morpholine (manufactured by Tokyo Chemical Industry Co., Ltd.), 0.5 parts of methylenebisacrylamide (manufactured by Tokyo Chemical Industry Co., Ltd.), and 120 parts of glycerin (manufactured by Tokyo Chemical Industry Co., Ltd.) were added to the thus-obtained liquid dispersion.

Thereafter, 1 part of tetramethylethylenediamine (manufactured by FUJIFILM Wako Pure Chemical Corporation) was added while being cooled in an ice bath. After mixing and stirring, degassing under a reduced pressure was conducted for 10 minutes. Subsequently, the resultant was subjected to filtration to remove impurities, etc. to obtain a homogeneous liquid material 1 for forming a phantom.

Preparation Example 2

Preparation of Cyan Pigment Liquid Dispersion

After through replacement with nitrogen gas in a flask equipped with a mechanical stirrer, a thermometer, a nitrogen gas introducing tube, a reflux tube, and a dripping funnel, 11.2 g of styrene, 2.8 g of acrylic acid, 12.0 g of lauryl methacrylate, 4.0 g of polyethylene glycol methacrylate, 4.0 g of styrene macromer, and 0.4 g of mercapto ethanol were admixed in the flask and heated to 65 degrees C. Next, a mixed solution of 100.8 g of styrene, 25.2 g of acrylic acid, 108.0 g of lauryl methacrylate, 36.0 g of polyethylene glycol methacrylate, 60.0 g of hydroxyl ethyl methacrylate, 36.0 g of styrene macromer, 3.6 g of mercaptoethanol, 2.4 g of azobis methyl valeronitrile, and 18 g of methyl ethyl ketone was dripped into the flask in 2.5 hours. Thereafter, a mixed solution of 0.8 g of azobis methyl valeronitrile and 18 g of methyl ethyl ketone was dripped to the flask in 0.5 hours followed by aging at 65 degrees C. for one hour. Moreover, 0.8 g of azobismethylvaleronitrile was added. Subsequent to aging for one hour. 364 g of methyl ethyl ketone was added to the flask to obtain 800 g of a 50 percent by mass polymer solution.

Next, 28 g of the polymer solution, 42 g of the cyan pigment (C.I. Pigment Blue 15), 13.6 g of 1 mol/L potassium hydroxide aqueous solution, 20 g of methyl ethyl ketone, and 13.6 g of deionized water were thoroughly stirred followed by mix-kneading using a roll mill to obtain a paste. The thus-obtained paste was charged in 200 g of deionized water. Subsequent to through stirring, methylethyl ketone and water were distilled away using an evaporator. Furthermore, the resultant was subject to filtration under a pressure with a polyvinylidene fluoride membrane filter having an average pore diameter of 5.0 μm to obtain a cyan pigment liquid dispersion having a pigment proportion of 15 percent by mass and a solid portion proportion of 20 percent by mass.

Preparation of Liquid Material 2 for Forming Phantom

While stirring 120 parts of deionized water, 1.7 parts of synthetic hectorite (Laponite XLG, manufactured by Rockwood Additives Ltd.) having a composition of [$Mg_{5.34}Li_{0.66}Si_8O_{20}(OH)_4$] $Na^-_{0.66}$ as a mineral was added to the deionized water little by little and 0.1 parts of 1-hydroxyethane-1,1-diphosphonic acid was further added thereto followed by stirring to prepare a liquid dispersion.

Next, 1 part of N, N-dimethylacrylamide as a polymerizable monomer (manufactured by FUJIFILM Wako Pure Chemical Corporation) which was caused to pass through a column of activated alumina to remove the polymerization inhibitor, 5 parts of acryloyl morpholine (manufactured by Tokyo Chemical Industry Co., Ltd.), 0.1 parts of methylenebisacrylamide (manufactured by Tokyo Chemical Industry Co., Ltd.), and 20 parts of glycerin (manufactured by Tokyo Chemical Industry Co., Ltd.) were added to the thus-obtained liquid dispersion.

Next, while being cooled in an ice bath, 1 part of tetramethylethylenediamine (manufactured by FUJIFILM Wako Pure Chemical Corporation), 3 parts of silica (Aerosil 200, manufactured by Nippon Aerosil Co., Ltd.), and 0.2 parts of the thus-prepared cyan pigment liquid dispersion were added. Subsequent to stirring and mixing, the mixture was degassed under a reduced pressure for 10 minutes. Subsequently, the resultant was subjected to filtration to remove impurities, etc. to obtain a homogeneous liquid material 2 for forming a phantom.

Example 1

Method of Manufacturing Ultrasonic Inspection Phantom

Manufacturing of Phantom (Tumor Part)

A mold was prepared capable of fabricating ten spherical tumor parts having a diameter of 20 mm at the same time.

4 parts of 2 percent by mass deionized water aqueous solution of peroxo sodium disulfate (manufactured by FUJIFILM Wako Pure Chemical Corporation) was added to 50 parts of the liquid material 2 for forming a phantom. Subsequent to through stirring, the mixture was poured into the mold and sealed with the lid followed by curing reaction at 25 degrees C. for two hours.

After curing, the resultant was taken out from the mold and rinsed to obtain a tumor part having a diameter of 20 mm.

Manufacturing of Phantom (Normal Part)

A cylindrical mold as shown in FIG. 3 was prepared and the tumor part prepared as described above was set floating in the air.

2.5 parts of 2 percent by mass deionized water aqueous solution of peroxo sodium disulfate (manufactured by FUJIFILM Wako Pure Chemical Corporation) was added to 30 parts of the liquid material 1 for forming a phantom. Subsequent to through stirring, the mixture was poured into the mold and sealed with the lid followed by curing reaction at 25 degrees C. for two hours.

After curing, the resultant was taken out of the mold and rinsed to obtain a cylindrical ultrasonic inspection phantom 103 enclosing the spherical tumor part 104 having a diameter of 20 mm inside (FIG. 5).

Example 2

An ultrasonic inspection phantom was manufactured in the same manner as in Example 1 except that silica (Aerosil® 200V, manufactured by Nippon Aerosil Co., Ltd.) was used instead of the silica (Aerosil® 200, manufactured by Nippon Aerosil Co., Ltd.) for use in the liquid material 2 for forming a phantom.

Example 3

An ultrasonic inspection phantom was manufactured in the same manner as in Example 1 except that silica (Aerosil® OX50, manufactured by Nippon Aerosil Co., Ltd.) was used instead of the silica (Aerosil® 200, manufactured by Nippon Aerosil Co., Ltd.) for use in the liquid material 2 for forming a phantom.

Example 4

An ultrasonic inspection phantom was manufactured in the same manner as in Example 1 except that silica (Aerosil® 90G, manufactured by Nippon Aerosil Co., Ltd.) was used instead of the silica (Aerosil® 200, manufactured by Nippon Aerosil Co., Ltd.) for use in the liquid material 2 for forming a phantom.

Example 5

An ultrasonic inspection phantom was manufactured in the same manner as in Example 1 except that silica (Aerosil® 50, manufactured by Nippon Aerosil Co., Ltd.) was used instead of the silica (Aerosil® 200, manufactured by Nippon Aerosil Co., Ltd.) for use in the liquid material 2 for forming a phantom.

Example 6

An ultrasonic inspection phantom was manufactured in the same manner as in Example 1 except that silica (Aerosil® MOX170, manufactured by Nippon Aerosil Co., Ltd.) was used instead of the silica (Aerosil® 200, manufactured by Nippon Aerosil Co., Ltd.) for use in the liquid material 2 for forming a phantom.

Example 7

An ultrasonic inspection phantom was manufactured in the same manner as in Example 1 except that titanium oxide (Aerosil® P25, manufactured by Nippon Aerosil Co., Ltd.) was used instead of the silica (Aerosil® 200, manufactured by Nippon Aerosil Co., Ltd.) for use in the liquid material 2 for forming a phantom.

Example 8

An ultrasonic inspection phantom was manufactured in the same manner as in Example 1 except that alumina (Aerosil® AluC, manufactured by Nippon Aerosil Co., Ltd.) was used instead of the silica (Aerosil® 200, manufactured by Nippon Aerosil Co., Ltd.) for use in the liquid material 2 for forming a phantom.

Evaluation 1

Echo images of the ultrasonic inspection phantoms manufactured in Examples 1 to 8 were observed with an ultrasonic observation device for endoscopes (EU-ME 2, manufactured by Olympus Corporation).

Figure 9:
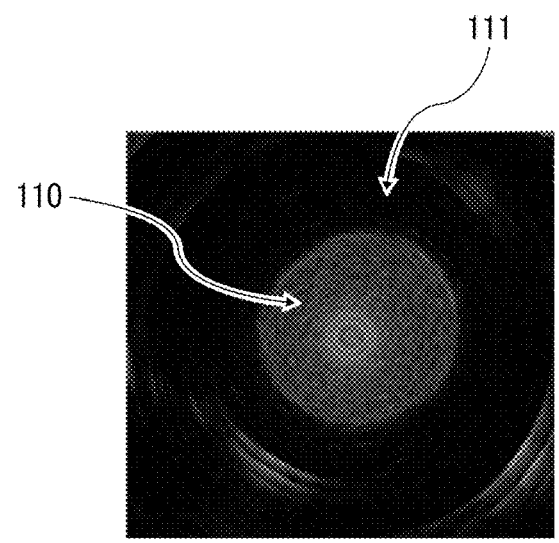
FIG. 9 is an ultrasonic image of the ultrasonic inspection phantom fabricated in Example 1 described later.

FIG. 9 is an echo image of the ultrasonic inspection phantom manufactured in Example 1. The echo image illustrated in FIG. 9 was distinctive and clear having an extremely wide contrast between a normal part 111 and a tumor part 110.

Figure 10:
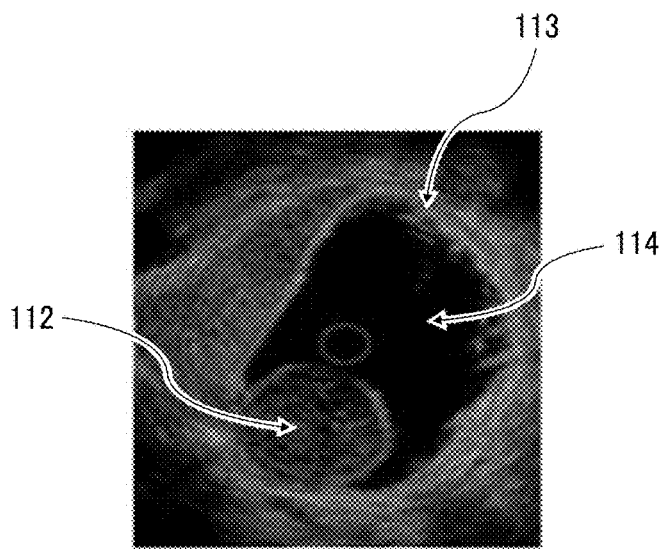
FIG. 10 is an ultrasonic image of a state in which a tumor is formed inside the stomach of a human body.

FIG. 10 is an echo image of the diseased part of a tumor caused in a human stomach. As seen in FIG. 10, a stomach wall 113, a tumor 112 formed inside the stomach, and the space (filled with gastric juice) of a stomach interior 114 had a contrast in the echo image, which was reproduced in the echo image of the phantom illustrated in FIG. 9.

The echo images of the ultrasonic inspection phantoms of Examples 2 to 8 were similar and the contrasts were evaluated. The image contrasts were evaluated according to the following index. The results are shown in Table 1.

Evaluation Index

S: Contrast between the normal part and the tumor part is clear and the tumor part is reproduced in white to gray A: Contrast between the normal part and the tumor part is distinctive and the tumor part is reproduced in pale gray B: No contrast between the normal part and tumor part and the tumor part is reproduced in black Evaluation 2

Whether biopsy by puncture for the tumor part was possible was determined by a puncture aspiration test. The results were evaluated according to the following index. The results are shown in Table 1.

Evaluation Index

A: Sufficiently collected

B: Impossible to collect

TABLE 1

Metal oxide added to tumor part

| | Kind | Specific surface area (m²/g) | Echo image | Puncture result |
|---|---|---|---|---|
| Example 1 | Silica | 200 | S | A |
| Example 2 | Silica | 200 | S | A |
| Example 3 | Silica | 50 | A | A |
| Example 4 | Silica | 90 | A | A |
| Example 5 | Silica | 50 | A | A |
| Example 6 | Alumina-containing silica | 170 | S | A |
| Example 7 | Titanium Oxide | 50 | A | A |
| Example 8 | Alumina | 100 | A | A |

* The BET method was used to obtain the specific surface area of the metal oxide.

Comparative Examples 1 to 3

Ultrasonic inspection phantoms were manufactured according to Example 1 disclosed in JP-4648310-B1.

Manufacturing of Phantom (Tumor Part)

The tumor part enclosed in the phantom was manufactured in the same manner as in Example 1 of the present disclosure using the following three compositions.

(A): A liquid dispersion of 9 mL of acrylamide stock solution (390 g of acrylamide and 10 g of N, N'-methylenebisacrylamide diluted up to 1,000 mL total with distilled water) and 1 g of titanium oxide particulates diluted in a measuring cylinder to 25 ml total (B): Liquid dispersion of 9 mL of acrylamide stock solution and 0.6 g of titanium oxide particulates diluted up to 25 mL with distilled water (C): Liquid dispersion of 9 mL of acrylamide stock solution and 0.01 g of titanium oxide particulates diluted up to 25 mL with distilled water These three kinds of liquid dispersions were degassed while being stirred for five minutes each. 0.25 mL of ammonium persulfite (APS) and 0.01 mL of N,N,N',N',-tetramethylethylene diamine (TEMDE) were added thereto. The mixture was poured into the mold having a diameter of 20 mm used in Example 1 and gelated with the lid closed to manufacture three kinds of tumor parts.

Manufacturing of Phantom (Normal Part)

80 mL of a 40 percent by mass acrylamide stock solution (390 g of acrylamide and 10 g of N,N'-methylenebisacrylamide diluted up to 1,000 mL total with distilled water) and 12.5 g of titanium oxide particulates (P-25, manufactured by Nippon Aerosil Co., Ltd.) were diluted up to 500 mL with distilled water followed by degassing for 30 minutes while being stirred.

5 mL of 10 percent by mass ammonium persulfate (APS) and 0.2 mL of N,N,N',N',-tetramethylethylene diamine (TEMED) were added thereto to prepare a liquid material for forming a phantom.

The three kinds of the tumor parts manufactured in advance were set in the cylindrical mold 102 used in Example 1 as illustrated in FIG. 3 and the prepared liquid material for forming a phantom was poured into the mold 102 and gelated with the lid closed to manufacture each of the three kinds of phantoms.

Evaluation

The phantoms manufactured in Examples 1 and 7 and Comparative Examples 1 to 3 were evaluated in the same manner as in Evaluation 1 and Evaluation 2.

After being subjected to the test of Evaluation 2, the phantom was hermetically stored at 22 degrees C. and 50 percent RH environment for one week and the echo image was observed again in the same manner as in Evaluation 1. The index of the echo images after the storage is as follows:
Evaluation Index
A: Signs caused by puncture disappeared
B: Signs caused by puncture remained

TABLE 2

|  | Echo image | Puncture result | Echo image after storage |
|---|---|---|---|
| Example 1 | S | A | A |
| Example 7 | A | A | A |
| Comparative Example 1 | A (Contrast is lower than contrast in Example 7) | A | B |
| Comparative Example 2 | A (Contrast is lower than contrast in Example 7) | A | B |
| Comparative Example 3 | A (Contrast is lower than contrast in Example 7) | A | B |

Example 9

In Example 9, an example of direct fabrication by a 3D printer is described. Preparation of Liquid Material 3 for Forming Phantom First, 17 parts of synthesized hectorite (laponite XLG, manufactured by Rockwood Additives Ltd.) having a composition of $[Mg_{5.34}Li_{0.66}Si_8O_{20}(OH)_4]Na^-_{0.66}$ as the water swellable laminate clay mineral was added little by little to 165 parts of pure water while stirring the pure water followed by stiffing three hours to prepare a liquid dispersion. Thereafter, 0.7 parts of 1-hydroxyethane-1,1-diphosphonic acid (manufactured by TOKYO CHEMICAL INDUSTRY CO., LTD.) was added and further stirred for one hour. Thereafter, 30 parts of glycerin (manufactured by Sakamoto Yakuhin Kogyo Co., Ltd.) was added and stirred for 10 minutes.

Next, 17 parts of acroyl morpholine (manufactured by KJ Chemicals Corporation) as a polymerizable monomer which was caused to pass through a column of activated alumina to remove the polymerization inhibitor, 4 parts of N, N-dimethylacrylamide (manufactured by FUJIFILM Wako Pure Chemical Corporation), and 0.7 parts of methylenebisacrylamide (manufactured by Tokyo Chemical Industry Co., Ltd.) were added to the thus-obtained liquid dispersion. Furthermore, 1 part of EMALGEN SLS-106 (manufactured by Kao Corporation) serving as surfactant was admixed with the resultant.

Next, while cooling the mixture in an ice bath, 2.4 parts of a 4 percent by mass methanol solution of a photopolymerization initiator (Irgacure 184, manufactured by BASF Corporation) was added, stirred and mixed, and thereafter degassed under a reduced pressure for 20 minutes. Subsequently, the resultant was subjected to remove impurities, etc. to obtain a liquid material 3 for forming a phantom.

Preparation of Liquid Material 4 for Forming Phantom

First, 17 parts of synthesized hectorite (laponite XLG, manufactured by Rockwood Additives Ltd.) having a composition of $[Mg_{5.34}Li_{0.66}Si_8O_{20}(OH)_4]Na^-_{0.66}$ as the water swellable laminate clay mineral was added little by little to 165 parts of pure water while stirring the pure water followed by stirring three hours to prepare a liquid dispersion. Thereafter, 0.7 parts of 1-hydroxyethane-1,1-diphosphonic acid (manufactured by TOKYO CHEMICAL INDUSTRY CO., LTD.) was added and further stirred for one hour. Thereafter, 30 parts of glycerin (manufactured by Sakamoto Yakuhin Kogyo Co., Ltd.) was added and stirred for 10 minutes.

Next, 17 parts of acroyl morpholine (manufactured by KJ Chemicals Corporation) as a polymerizable monomer which was caused to pass through a column of activated alumina to remove the polymerization inhibitor, 4 parts of N, N-dimethylacrylamide (manufactured by FUJIFILM Wako Pure Chemical Corporation), and 0.7 parts of methylenebisacrylamide (manufactured by Tokyo Chemical Industry Co., Ltd.) were added to the thus-obtained liquid dispersion. Furthermore, 1 part of EMALGEN SLS-106 (manufactured by Kao Corporation) serving as surfactant was admixed with the resultant.

Furthermore, 1 part by mass of silica (Aerosil 200, manufactured by Nippon Aerosil Co., Ltd.) was admixed by stirring.

Next, while cooling the mixture in an ice bath, 2.4 parts of a 4 percent by mass methanol solution of a photopolymerization initiator (Irgacure 184, manufactured by BASF Corporation) was added, stirred and mixed, and thereafter degassed under a reduced pressure for 20 minutes. Subsequently, the resultant was subjected to remove impurities, etc. to obtain a liquid material 4 for forming a phantom.

Preparation of Liquid Material 5 for Forming Phantom

First, 17 parts of synthesized hectorite (laponite XLG, manufactured by Rockwood Additives Ltd.) having a composition of $[Mg_{5.34}Li_{0.66}Si_8O_{20}(OH)_4]Na^-_{0.66}$ as the water swellable laminate clay mineral was added little by little to 165 parts of pure water while stirring the pure water followed by stirring three hours to prepare a liquid dispersion. Thereafter, 0.7 parts of 1-hydroxyethane-1,1-diphosphonic acid (manufactured by TOKYO CHEMICAL INDUSTRY CO., LTD.) was added and further stirred for one hour. Thereafter, 30 parts of glycerin (manufactured by Sakamoto Yakuhin Kogyo Co., Ltd.) was added and stirred for 10 minutes.

Next, 17 parts of acroyl morpholine (manufactured by KJ Chemicals Corporation) as a polymerizable monomer which was caused to pass through a column of activated alumina to remove the polymerization inhibitor, 4 parts of N, N-dimethylacrylamide (manufactured by FUJIFILM Wako Pure Chemical Corporation), and 0.7 parts of methylenebisacrylamide (manufactured by Tokyo Chemical Industry Co., Ltd.) were added to the thus-obtained liquid dispersion. Furthermore, 1 part of EMALGEN SLS-106 (manufactured by Kao Corporation) serving as surfactant was admixed with the resultant.

Furthermore, 3 parts by mass of silica (Aerosil 200, manufactured by Nippon Aerosil Co., Ltd.) was admixed by stirring.

Next, while cooling the mixture in an ice bath, 2.4 parts of a 4 percent by mass methanol solution of a photopolymerization initiator (Irgacure 184, manufactured by BASF Corporation) was added, stirred and mixed, and thereafter degassed under a reduced pressure for 20 minutes. Subsequently, the resultant was subjected to remove impurities, etc. to obtain a liquid material 5 for forming a phantom.

Preparation of Liquid Material for Forming Support

The following recipe was dispersed using a homogenizer (HG30, manufactured by Hitachi Koki Co., Ltd.) at 2,000 rotation per minute (rpm) until a homogenized mixture was obtained Urethane acrylate (Diabeam UK6038, manufactured by Mitsubishi Chemical Corporation): 10 parts Neopentyl glycol hydroxy pivalic acid ester di(meth) acrylate (polymerizable monomer, KAYARAD MANDA, manufactured by Nippon Kayaku Co., Ltd.): 90 parts 1-hydroxycyclohexyl phenylketon (polymerization initiator, IRGACURE® 184, manufactured by BASF SE): 3 parts.

Thereafter, the mixture was filtered to remove impurities followed by vacuum degassing for ten minutes to obtain a homogenized liquid material for forming a support.

Fabrication by 3D Printer

The four ink heads (GEN4, manufactured by Ricoh Industry Company, Ltd.) of the 3D printer employing an inkjet method as illustrated in FIG. 6 were filled with the liquid material 3 for forming a phantom, the liquid material 4 for forming a phantom, the liquid material 5 for forming a phantom, and the liquid material for forming a support and jetted these liquid materials to form layers.

Based on the CT data indicating the state of the tumor formed inside a kidney of the human body, the CT data was converted into data for 3D print to fabricate a kidney-type phantom based on this. The ureter part was fabricated by the liquid material 3 for forming a phantom, the normal part was fabricated by the liquid material 4 for forming a phantom, the tumor part was fabricated by the liquid material 5 for forming a phantom, and the support for these parts was fabricated by the liquid material for forming a support to fabricate a phantom.

The liquid material 3 for forming a phantom, the liquid material 4 for forming a phantom, the liquid material 5 for forming a phantom, and the liquid material for forming a support were hardened with 350 mJ/cm² of light intensity emitted from an ultraviolet irradiator (SPOT CURE SP 5-250 DB, manufactured by Ushio Inc.) to form a phantom and a support.

Figure 11:
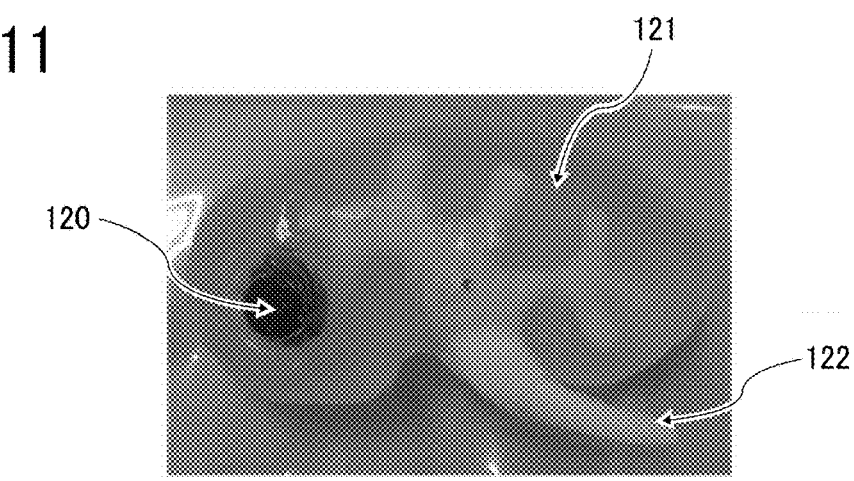
FIG. 11 is a diagram illustrating an ultrasonic inspection phantom of kidney type directly fabricated by a 3D printer.

After the fabrication, as illustrated in FIG. 7, the phantom 17 and the support 18 were peeled off from each other to manufacture a kidney-type phantom as illustrated in FIG. 11. The reference numeral 120 denotes a tumor portion, 121 denotes a normal portion, and 122 denotes a ureter in FIG. 11.

Evaluation

The echo image of the thus-manufactured kidney-type phantom was observed using an endoscopic ultrasonic device EU-ME2 (manufactured by Olympus Corporation) in the same manner as in Evaluation 1. The results are shown in FIG. 12.

Figure 12:
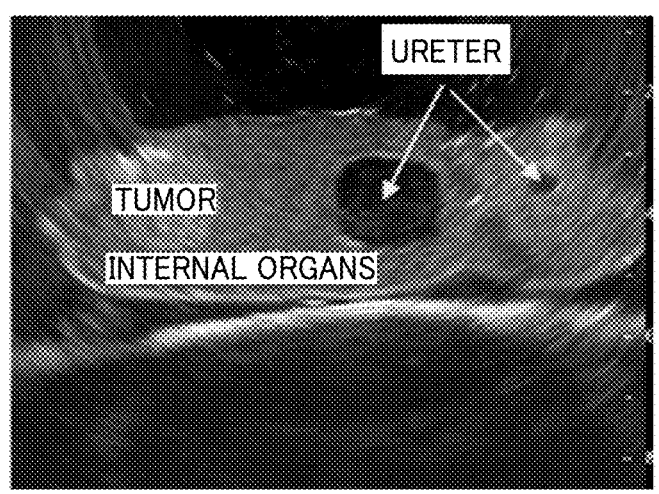
FIG. 12 is an ultrasonic image of the ultrasonic inspection phantom of kidney type illustrated in FIG. 11.

As seen in FIG. 12, a contrast between the tumor part and the normal part was obtained so that the tumor part was able to be identified. In addition, the ureter, which has a hollow structure, appeared black like a human body, which indicated that the kidney-type phantom was formed true to life.

The aspects of the present disclosure are, for example, as follows:

1. An ultrasonic inspection phantom includes a hydrogel including water, a polymer, and a mineral.
2. The ultrasonic inspection phantom according to 1 mentioned above, wherein the water is enclosed in the three-dimensional network structure formed by combining the polymer and the mineral.
3. The ultrasonic inspection phantom according to 1 or 2 mentioned above, further includes a metal oxide having a specific surface area of 50 m²/g or greater.
4. The ultrasonic inspection phantom according to 3 mentioned above, wherein the metal oxide includes silica.
5. The ultrasonic inspection phantom according to 3 mentioned above, wherein the metal oxide includes alumina-containing silica.
6. The ultrasonic inspection phantom according to any one of 1 to 5 mentioned above, further includes a pseudo lesion mimicking a lesion caused in a living tissue.
7. The ultrasonic test phantom according to 6 mentioned above, wherein ultrasonic propagation in the pseudo lesion is slower than in the ultrasonic test phantom excluding the pseudo lesion.
8. The ultrasonic inspection phantom according to 7 mentioned above, wherein the pseudo lesion contains a metal oxide having a specific surface area of 150 m²/g or greater.
9. The ultrasonic inspection phantom according to 8 mentioned above, wherein the metal oxide includes silica.
10. The ultrasonic inspection phantom according to 8 mentioned above, wherein the metal oxide includes alumina-containing silica.
11. The ultrasonic inspection phantom according to any one of 1 to 10 mentioned above having a self-healing property.
12. The ultrasonic inspection phantom according to any one of 1 to 11 mentioned above for use in training for puncture treatment of ultrasonic inspection.
13. A method of manufacturing an ultrasonic inspection phantom using a liquid material for forming a phantom containing a hydrogel containing water, a polymer, and a mineral.
14. The method according to 13 mentioned above, wherein the liquid material for forming a phantom contains a metal oxide having a specific surface area of 50 m²/g or greater.
15. The method according to 14 mentioned above, wherein the metal oxide includes silica.
16. The method according to 14 mentioned above, wherein the metal oxide includes alumina-containing silica.
17. The method according to any one of 13 to 16 mentioned above, wherein the liquid material for forming a phantom contains a polymerization initiator.
18. The method according to any one of 13 to 17 mentioned above, wherein the liquid material for forming a phantom is poured into a mold and hardened therein.
19. The method according to 18 mentioned above, wherein the mold is manufactured by a 3D printer.
20. The method according to any one of 13 to 17 mentioned above, wherein, using the liquid material for forming a phantom, the phantom is formed by a 3D printer.
21. The method according to 18 mentioned above, wherein the 3D printer employs an inkjet method or stereolithography.

Having now fully described embodiments of the present invention, it will be apparent to one of ordinary skill in the art that many changes and modifications can be made thereto without departing from the spirit and scope of embodiments of the invention as set forth herein.

What is claimed is:

1. An ultrasonic inspection phantom, comprising:
    a hydrogel comprising water, a polymer, and a water swellable laminate clay mineral,
    wherein the water swellable laminate clay mineral is included in an amount of from 1 to 7.15 percent by mass to a total amount of the ultrasonic inspection phantom, and
    the water is enclosed in a three-dimensional network structure of a complex combination of the polymer and the water swellable laminate clay mineral.

2. The ultrasonic inspection phantom according to claim 1, further comprising:
a metal oxide having a specific surface area of 50 m²/g or greater.

3. The ultrasonic inspection phantom according to claim 2, wherein the metal oxide comprises silica.

4. The ultrasonic inspection phantom according to claim 2, wherein the metal oxide comprises alumina-containing silica.

5. The ultrasonic inspection phantom according to claim 1, wherein the ultrasonic inspection phantom includes a pseudo lesion mimicking a lesion caused in a living tissue.

6. The ultrasonic inspection phantom according to claim 5, wherein ultrasonic propagation in the pseudo lesion is slower than in the ultrasonic inspection phantom excluding the pseudo lesion.

7. The ultrasonic inspection phantom according to claim 6, wherein the pseudo lesion comprises a metal oxide having a specific surface area of 150 m²/g or greater.

8. The ultrasonic inspection phantom according to claim 7, wherein the metal oxide comprises silica.

9. The ultrasonic inspection phantom according to claim 7, wherein the metal oxide comprises alumina-containing silica.

10. The ultrasonic inspection phantom according to claim 1, wherein the ultrasonic inspection phantom has a self-healing property.

11. A method for training for puncture treatment of ultrasonic inspection, the method comprising:
performing an ultrasonic inspection, puncture treatment, or both, on the ultrasonic inspection phantom according to claim 1.

12. A method of manufacturing the ultrasonic inspection phantom of claim 1, the method comprising:
forming the ultrasonic inspection phantom using a liquid material.

13. The method according to claim 12, wherein the forming of the ultrasonic inspection phantom comprises casting the liquid material into a mold, and hardening the liquid material.

14. The method according to claim 12, wherein the forming of the ultrasonic inspection phantom comprises fabricating the ultrasonic inspection phantom by a 3D printer using the liquid material.

15. The method according to claim 14, wherein the 3D printer employs an inkjet method or stereolithography.

16. The ultrasonic inspection phantom according to claim 1, wherein the water swellable laminate clay mineral comprises at least one selected from the group consisting of water swellable smectite and water swellable mica.

17. The ultrasonic inspection phantom according to claim 1, wherein the water swellable laminate clay mineral comprises at least one selected from the group consisting of water swellable hectorite, water swellable montmorillonite, water swellable saponite, and water swellable synthesized mica.

18. The ultrasonic inspection phantom according to claim 1, wherein the water swellable laminate clay mineral is included in an amount of from 1 to 7.06 percent by mass to a total amount of the ultrasonic inspection phantom.

19. The ultrasonic inspection phantom according to claim 1, wherein the ultrasonic inspection phantom includes a pseudo lesion mimicking a lesion caused in a living tissue, and a non-pseudo lesion,
the pseudo lesion comprises a metal oxide comprising silica having a specific surface area of 150 m²/g or greater, and
the non-pseudo lesion does not comprise the metal oxide.

20. The ultrasonic inspection phantom according to claim 1, wherein the polymer has at least one group selected from the group consisting of an amide group, an amino group, a hydroxyl group, a tetramethyl ammonium group, a silanol group, and an epoxy group.

21. The ultrasonic inspection phantom according to claim 1, wherein the polymer is a polymerized product of at least one polymerizable monomer selected from the group consisting of acrylamides, N-substituted acrylamide derivatives, N,N-di-substituted acrylamide derivatives, N-substituted methacrylamide derivatives, N,N-di-substituted methacrylamide derivatives, 2-etylhexyl(meth)acrylate (EHA), 2-hydroxyethyl(meth)acrylate (HEA), 2-hydroxypropyl(meth)acrylate (HPA), acryloyl morpholine (ACMO), caprolactone-modified tetrahydrofurfuryl(meta)acrylate, isobonyl(meth)acrylate, 3-methoxybutyl(meth)acrylate, tetrahydro furfuryl (meth)acrylate, lauryl(meth)acrylate, 2-phenoxyethyl (meth)acrylate, isodecyl(meth)acrylate, isooctyl(meth)acrylate, tridecyl(meth)acrylate, caprolactone(meth)acrylate, ethoxyfied nonylphenol(meth)acrylate, and urethane(meth)acrylate.

* * * * *